(12) United States Patent
Pelletier (10) Patent No.: US 7,587,331 B2
(45) Date of Patent: Sep. 8, 2009

(54) SYSTEM AND METHOD FOR DETERMINING A SCENT OR TASTE PROFILE FOR PREDICTING A USER ADAPTED SCENT OR TASTE

(75) Inventor: Olivier Pelletier, Zurich (CH)

(73) Assignee: Accenture Global Services GmbH (CH)

( * ) Notice: Subject to any disclaimer, the term of this patent is extended or adjusted under 35 U.S.C. 154(b) by 1111 days.

(21) Appl. No.: 10/615,157

(22) Filed: Jul. 7, 2003

(65) Prior Publication Data

US 2004/0107053 A1 Jun. 3, 2004

(30) Foreign Application Priority Data

Jul. 12, 2002 (EP) ................................. 02354109

(51) Int. Cl.
G06F 17/30 (2006.01)
G07G 1/00 (2006.01)
(52) U.S. Cl. ...................................................... 705/10
(58) Field of Classification Search .................... 705/10
See application file for complete search history.

(56) References Cited

U.S. PATENT DOCUMENTS

| | | | | |
|---|---|---|---|---|
| 5,200,909 A | * | 4/1993 | Juergens | ....................... 702/25 |
| 5,302,262 A | | 4/1994 | Yamafuji et al. | |
| 6,606,566 B1 | * | 8/2003 | Sunshine | ....................... 702/22 |
| 7,003,515 B1 | * | 2/2006 | Glaser et al. | ..................... 707/5 |
| 7,103,592 B2 | * | 9/2006 | Huret | ............................. 707/3 |
| 2005/0038819 A1 | * | 2/2005 | Hicken et al. | ............. 707/104.1 |

FOREIGN PATENT DOCUMENTS

| | | |
|---|---|---|
| DE | 100 65545 A1 | 7/2002 |
| JP | 63241354 | 10/1988 |
| JP | 05099896 | 4/1993 |
| JP | 2000-019137 A | 1/2000 |
| JP | 2000019137 | 1/2000 |
| JP | 2001184356 | 7/2001 |
| WO | WO 01/07093 | * 2/2001 |

OTHER PUBLICATIONS

Hillier, Frederick S., and Gerald J. Lieberman. Introduction to Operations Research. 6th ed. McGraw-Hill, 1995. pp. 497-503 and 586-591.*

(Continued)

*Primary Examiner*—Beth V Boswell
*Assistant Examiner*—Folashade Anderson
(74) *Attorney, Agent, or Firm*—Brinks Hofer Gilson & Lione (57) ABSTRACT

The invention concerns a method and a system for determining a scent or taste profile of a user consisting in: storing for each of a set of products chosen among products for which a database contains smell of taste prints constituted by a set of measurements given by smell or taste electronic sensors, a rating (SN) given by the user; and automatically calculating weighting coefficients constituting said profile and respectively affected to said sensors, by successive approximation of sets of weighting coefficients leading to minimizing the sum of the quadratic errors over the set of satisfaction notes.

17 Claims, 2 Drawing Sheets

OTHER PUBLICATIONS

Savage Beast Technologies Unleashes New Music Search and Recommendation Technology That Maps Genetic Makeup of Music to an Individual's Taste. (Nov. 13). PR Newswire,1. Retrieved Dec. 6, 2007, from Business Dateline database. (Document ID: 63644132).*

Louis Jacobson (Mar. 22, 1999). Artificial Tongue Has a Taste for Many Tasks :[Final Edition]. The Washington Post,p. A09. Retrieved Dec. 6, 2007, from Business Dateline database. (Document ID: 39924152).*

Hillier, Frederick S., and Gerald J. Lieberman. Introduction to Operations Reasearch. 6th ed. McGraw-Hill, 1995. pp. 820-827.*

Gutierrez-Osuna, R., et al., "Correlation of Sensory Analysis with Electronic Nose Data for Swine Odor Remediation Assesment," Proceedings of the $3^{rd}$ European Congress on Odours, Metrology and Electronic Noses, Paris, France, Jun. 19-21, 2001.

Giese, James, "Electronic Noses," Ford Technology, vol. 54, No. 3, pp. 96-100, Mar. 2000.

Pescovitz, David, "This Nose Knows," Wired Magazine, Issue 7.12, Dec. 1999.

Sawyer, Abigail, "Technology Scent-sation Hi-Tech Devices Seek to Emulate," Wine Business Monthly, Jun. 2000.

Chin, Waynne W.—University of Houston, "Overview of the PLS Method," Oct. 18, 1997.

European Search Report mailed on Oct. 7, 2003, for EP patent application No. 02354109.7 filed on Jul. 12, 2002, 2 pgs.

* cited by examiner

SYSTEM AND METHOD FOR DETERMINING A SCENT OR TASTE PROFILE FOR PREDICTING A USER ADAPTED SCENT OR TASTE

This application claims the priority benefit of European Patent Application Serial No. 02354109.7, filed Jul. 12, 2002, titled "DETERMINING A SCENT OR TASTE PROFILE FOR PREDICTING A USER ADAPTED SCENT OR TASTE."

FIELD OF THE INVENTION

The present invention relates to a method and system for determining, among a set of olfactive or gustative products, a subset specifically enjoyed by a user. More particularly, the present invention concerns a method and system for determining the scent or taste profile of a user and a method and system for applying such a scent or taste profile to the determination of products the smell or taste of which are specifically adapted to this user.

An example of application of the present invention is to make recommendations of products for a dedicated user. For example, the invention may apply for recommending some perfumes to a user on the basis of his scent profile. Another example of application concerns proposing a wine selection to a user on the basis of his scent and/or taste profile.

BACKGROUND OF THE INVENTION

There are currently two solutions to make recommendations of products to a user.

A first one uses human experts that take advantage of their in-depth knowledge of the market to find products similar to the ones about which a given user has expressed preferences. Such a solution cannot be automated.

A second approach called "collaborative filtering" tries to find similarities between the opinions of different users and bases its predictions on the group behavior of users. Such an approach does not use relevant attributes of the product itself, which leads to errors in the recommendations.

The present invention aims at providing a new solution for making recommendations of products to a dedicated user.

Another purpose of the present invention is to provide an automatic system for establishing a profile for the scent or taste preferences of a given user, and to use this profile to make recommendations or to predict if this user will enjoy or not the smell or taste of a given product.

Another purpose of the present invention is to minimize the participation of the user in order to establish his profile.

Another purpose of the invention is to provide a method and system which is reliable and which does not take into account the opinions of other users to establish the profile of a given user.

Given that the present invention can be equally easily applied to the scent or taste of products, in the following, these characteristics of the products will simply be referred to as the sensory characteristics of the products. It is to be understood that this expression only encompasses the sense of olfaction or of taste, and is used as a convenient abbreviation.

BRIEF SUMMARY OF THE INVENTION

To attain these purposes and others, the present invention provides using scent or taste sensors called "electronic noses" or "electronic tongues" to acquire digital descriptions of a set of products, and to use these descriptions to establish a user profile and to predict products adapted for that user.

An electronic nose or tongue comprises a set of sensors and outputs a number (measurement) for each sensor. The set of all the measurements produced for a given product constitutes the smell or taste print (or signature) of that product. In the following, we will refer to either one of these as the sensory print of the product.

According to the present invention, the user is asked to rate the sensory characteristics of a set of products. These products are chosen among a database of sensory prints acquired previously by means of an electronic nose or tongue.

According to the present invention, the user's profile corresponds to a set of weighting coefficients attributed to measurements. These coefficients are used to calculate a predicted rating for a product not previously rated, based on its sensory print.

Having collected the ratings of the user, the system automatically determines the weighting coefficients of the user's profile. This is made by starting with an arbitrary set of weighting coefficients and using this set to predict the ratings of the products that have already been rated by the user. An error minimization method is applied to iteratively update these coefficients in order to obtain the best agreement between the predicted ratings and the expressed ratings. For example, a method known as X-square fitting consists in minimizing the sum of the quadratic differences between the expressed ratings and the predicted ratings (quadratic errors), by using the partial derivatives of this sum with respect to the weighting coefficients to update the weighting coefficients in a way that maximizes the sum at each step of the iteration. The set of weighting coefficients, for which the sum of quadratic errors is minimal, is considered as the profile of the user.

According to a preferred embodiment of the present invention, once the user has expressed a given number of ratings, the system automatically determines an additional product for which the user is asked to give an additional rating. Such an additional product is chosen as being the most relevant among the set of products to determine the weighting coefficients of the user.

Preferably, the number of satisfaction notes is comprised between 1 and 5, but could also be equal to 3 (like, indifferent, dislike).

For predicting the products preferred by a user inside the set of products, the present invention calculates, using the weighting coefficients of the user profile, an estimated satisfaction note for each product of this set, using the respective sensory prints of these products. Such a calculation consists, for each product, in summing the measurements comprising the sensory print respectively multiplied by the corresponding weighting coefficient of the user's profile, in order to obtain an estimated rating. Preferably, the estimated ratings are not rounded up/down to an integer value in order to increase the accuracy of the selection.

According to an embodiment, a subset of products close to the highest (or lowest) note with a predetermined margin is then outputted.

According to another embodiment, the number of the outputted products is predetermined.

BRIEF DESCRIPTION OF THE DRAWINGS

The foregoing and others purposes, features, aspects and advantages of the invention will become apparent from the following detailed description of embodiments, given by way of illustration and not limitation with reference to the accompanying drawings, among which.

For clarity, only the elements and steps useful to the understanding of the invention have been shown in the drawings and will be disclosed hereafter. Specifically, the programming steps according to the system of the invention will not be detailed as it will readily occur to those skilled in the art. Further, the invention will be disclosed in connection with a specific embodiment applied to perfumes. However, the invention applies more generally to any field in which predicting a product which might be liked or disliked by a user on the basis of his smell or taste profile can be useful.

DETAILED DESCRIPTION OF THE INVENTION

A first phase of the invention consists in creating a database containing scent or smell prints of different products.

According to a first embodiment, such smell prints are constituted by the smell prints of a set of perfumes for which the system has to give a prediction.

According to another embodiment, the smell prints correspond not only to perfumes but also to some basic products (for example, coffee, chocolate, a particular flower, a spice, etc.).

Figure 1:
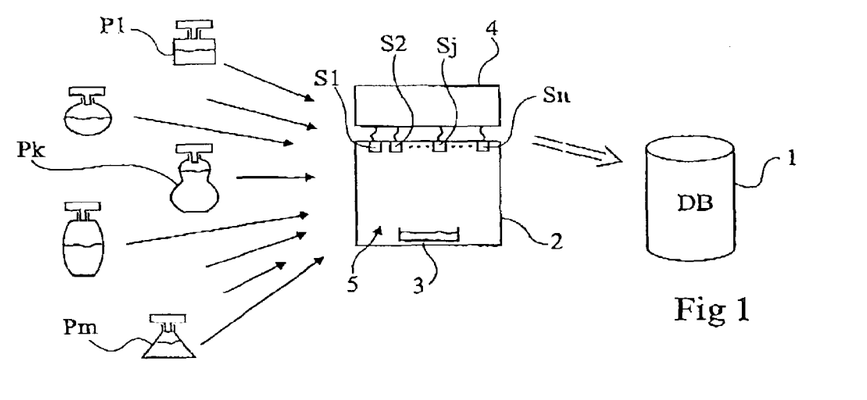
FIG. 1 schematically represents a system using an electronic nose for constituting a perfume smell print database according to an embodiment of the present invention.

FIG. 1 illustrates very schematically the first phase of the present invention according to a particular embodiment.

In this example, the smell prints used by the system are perfume smell prints. Therefore, the respective digital smell prints of a set of m perfumes $P_1, \ldots P_k, \ldots P_m$ have to fill a database 1. According to the invention, an electronic nose 2 is used to analyze successively a sample 3 of each perfume $P_k$ disposed in an analysis chamber 5.

Electronic noses are known devices based on an array of n chemical sensors $S_1, \ldots S_j, \ldots S_n$. Each sensor $S_j$ in the sensor array responds differently to a given chemical compound. In that way, it is possible to get a "smell print" for a given chemical compound or mixture (in this example, a perfume). This signature or print is a set of digital reading or measurements corresponding to the reading from the set of sensors. The number of sensors is usually comprised between 10 and 100, for example 32 or 64 depending on the desired accuracy. The scores given by the sensors are collected by a processing unit 4 of the electronic nose and stored in the database 1.

At the end of the acquisition phase of the invention, the database 1 contains, for each perfume $P_k$, an ordered set of n measurements corresponding to the smell signature or smell print of that perfume.

Preferably, the data acquisition made by the electronic nose 2 is not performed only once but, for a given product, several acquisitions (for example, between 5 and 40) are made. These data acquisitions serve to compute the smell signature taking into account the eventual dispersion of the sensed values for each sensor under varied acquisition conditions. Any conventional method used to take into account experimental dispersion of data acquisition (for example, a mean value) can be used for obtaining the n values comprising the smell print of each perfume $P_k$.

According to an exemplary embodiment of the invention, an electronic nose known under the commercial name "Cyranose 320", with 32 sensors, is used to obtain a set of perfume smell prints. According to this exemplary embodiment, each measurement comprising the smell print is a decimal value with seven significative figures.

The set of smell prints in the database can be updated by adding additional perfumes or other basic smell prints (coffee, chocolate, spice, etc.).

According to the present invention, the smell print's database is used to build a user's smell profile as it will be described hereafter. Such a smell or scent profile is, according to the present invention, to be used for predicting products (in this example, perfumes) that might be liked and/or disliked by the user.

Figure 2:
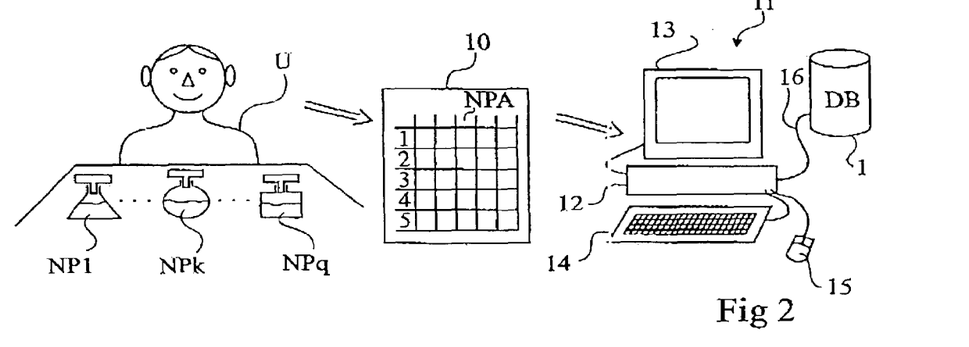
FIG. 2 schematically illustrates an embodiment for determining a scent profile of a user according to the present invention.

FIG. 2 schematically illustrates an embodiment of the present invention to establish a user profile for smell preferences.

The first step is to ask the user U to rate a subset of perfumes or, more generally, of products, according to their smell. In the disclosed embodiment, the user is asked to rate q perfumes among the set of m perfumes $P_k$. The rated perfumes are designated by $NP_h$ (h being comprised between 1 and q). According to the present invention, a small number of rated perfumes (less than 10) is enough to establish a user profile. Preferably, the system asks the user to rate between 3 and 8 perfumes.

The ratings given by the user have to be very selective, i.e. ranging from 1 to 5 or less. According to a preferred embodiment, the ratings given by the user range from 1 to 3: "like", "medium or indifferent" and "dislike". Eventually, a supplemental scale with two additional notes can be provided. Then, the possible notes are "like very much", "like", "medium", "dislike", "detest". The codes (digital values) that are attributed to each rating depend on the programmation of the system. Preferably, ratings are coded as 1, 2, 3, 4, 5 or 1, 2, 3.

The set of ratings (table 10, FIG. 2) is stored in a computerized system used to implement the invention. In FIG. 2, this system is symbolized as a personal computer 11 with a central unit 12, a screen 13, a keyboard 14 and a mouse 15. The central unit 12 is linked to the database 1 through a wired 16 or wireless link. For example, the database is contained in a web server (not shown) to be shared by several distant personal computers or systems implementing the method of the present invention.

Having collected the table 10 of q satisfaction notes from the user, the system computes a user profile, which is a set of weighting coefficients to be applied to each measurement of the smell prints of the m perfumes in a linear regression. The determination of the user profile will be better understood in connection with the description of FIG. 4.

According to a preferred embodiment of the invention, after having collected the ratings for q perfumes, the system automatically determines an additional perfume for which the rating given by the user will be significant for improving the determination of the list of weighting coefficients and asks the user to give an additional rating for this $NP_{q+1}$ perfume.

Once the user profile is established, the system according to the present invention is able to predict, among the set of all the m perfumes $P_k$ of the database 1, one or more perfumes about which the user is more likely to express positive ratings. Alternatively, the system can also predict the most disliked perfumes.

Figure 3:
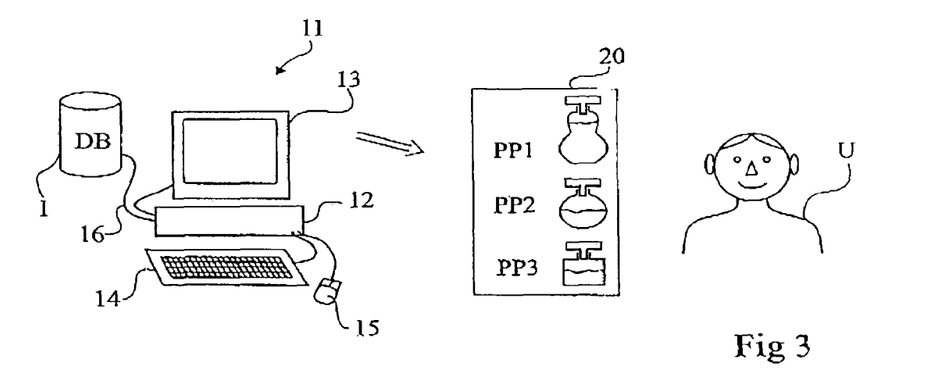
FIG. 3 schematically illustrates an embodiment of the system for predicting a subset of enjoyable perfumes for a user according to the present invention.

FIG. 3 illustrates, very schematically, an implementation of the method for predicting preferred perfumes according to the present invention. This method is preferably also implemented by the personal computer 11, which calculates, on the basis of the user profile, the satisfaction notes he would have given for the n perfumes $P_k$. For example, the system delivers three preferred perfumes PP1, PP2, PP3 in a list 20 to the user U. The list of preferred perfumes can be in this embodiment displayed on the screen 13 or printed out.

Figure 4:
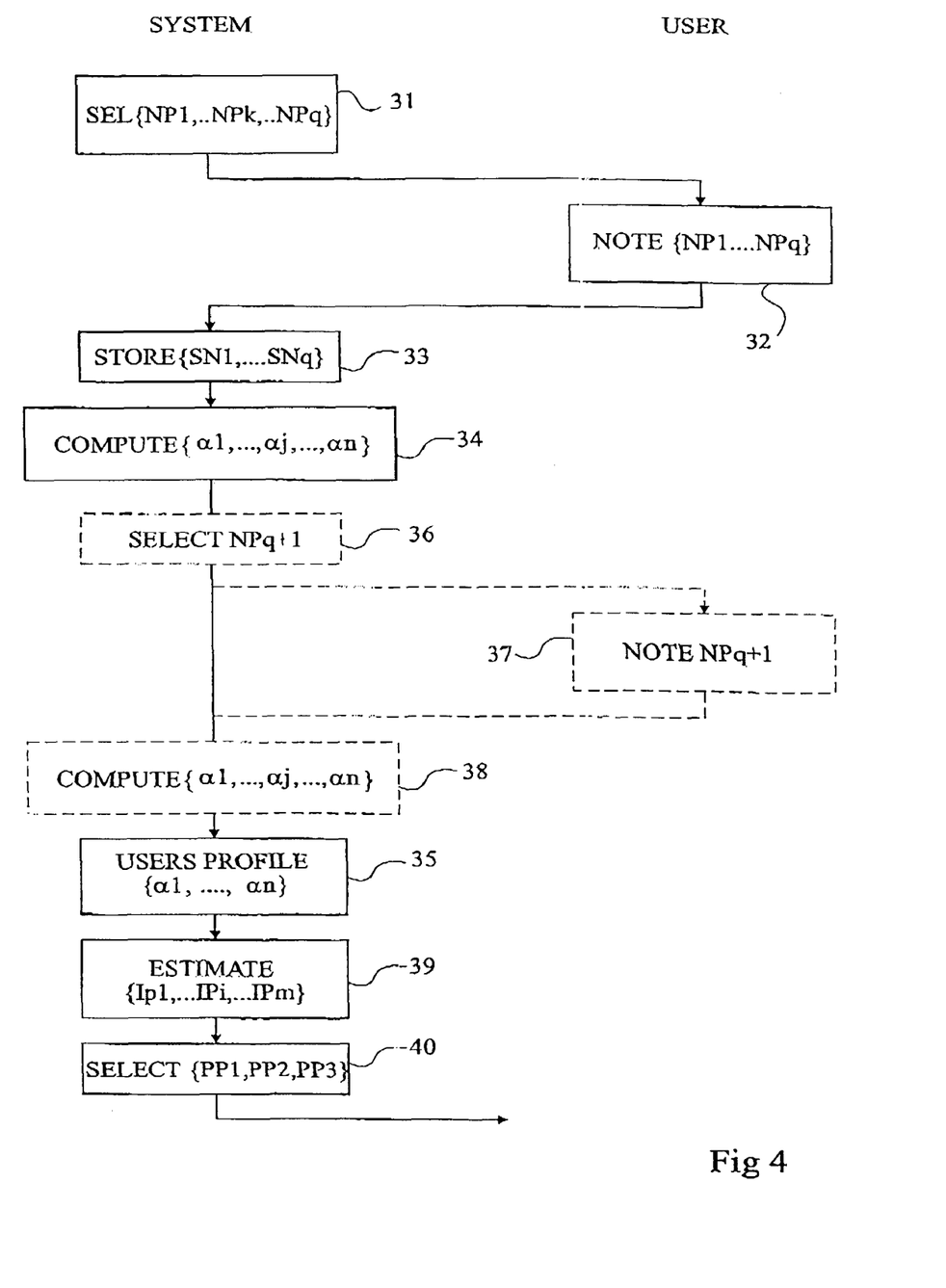
FIG. 4 is a flow chart schematically illustrating an embodiment of the method for determining a scent profile and for predicting a subset of enjoyable perfumes according to the present invention.

FIG. 4 represents a flowchart of an embodiment of the present invention showing the main steps of the method for establishing a user profile and predicting some preferred perfumes. In FIG. 4, the steps requiring the intervention of the user (USER) has been shown on the right side of the drawing, the steps automatically performed by the system (SYSTEM) have been shown on the left side of the drawing.

The first step (block 31) consists in selecting q perfumes $NP_h$ (h comprised between 1 and q) to be rated by the user. The performed notation can be a real notation, that is results from asking the user to smell a sample of perfume, or can be a virtual one, that is results from asking the user to quote some boxes displayed on the screen and representing satisfaction levels to the q perfumes, for example in an internet-based implementation of the invention. The set of selected perfumes to be noted can be chosen in different ways. A first solution consists, in a real mode evaluation, to leave the user choosing between 3 and 8 perfumes that he wants to note. A second solution is to randomizely select the q perfumes among those of the database 1. This solution more particularly applies to the internet-based implementation. A third solution is to pre-determine, among the list of m perfumes, q perfumes which are very different from the others on the basis of their respective smell prints.

Alternatively, the ratings can be automatically estimated on the basis of previous acquisitions of the user. For example, studying the more frequent perfumes acquired by a given user, it may be reasonably supposed that these perfumes have to be given the best notes. On the contrary, a perfume acquired only once by the user and no more for a long time can be assumed to be disliked.

The second step (block 32) is performed by the user when he gives a satisfaction note $SN_h$ (h comprised between 1 and q) to each of the q perfumes $NP_h$.

These satisfaction notes $SN_h$ are stored (block 33) in the system.

Then (block 34), the system computes n weighting coefficients $\alpha_j$ (j being comprised between 1 and n), where n corresponds to the number of sensors of the electronic nose (FIG. 1), that is of the readings taken into account for the smell prints.

According to an exemplary embodiment of the invention for which the scores are less than 0.1 and the number of scores is 32 per print, the weighting coefficients are numbers comprised between −10000 and +10000. The order of magnitude of the weighting coefficient is chosen in function of the number and order of magnitude of the scores to obtain notes in the desired range.

According to a preferred embodiment, the weighting coefficients are determined using an error minimization method, for example a method for minimizing the sum of the quadratic errors over the set of notes given by the user. This technique is known as X-square fitting. According to that example, the system proceeds by successive approximation of set of weighting coefficients $\alpha_j$ for minimizing the following formula:

$$\sum_{h=1}^{q}\left(SN_h - \sum_{j=1}^{n}(\alpha_j \cdot MV_{j,h})\right)^2,$$

where $MV_{j,h}$ designates the scores of rank j (sensor $S_j$) of the smell print of perfume of rank h. As disclosed above, $MV_{j,h}$ is preferably a mean value of several measurements.

According to a first embodiment, the user profile (block 35) is obtained after completion of the former step and corresponds to the set of coefficients $\alpha_j$ for which the above formula gives the minimal result.

According to a second preferred embodiment (illustrated in dotted lines in FIG. 4), step 34 is followed by a step (block 36) of selection of an additional perfume $P_{q+1}$ to be noted by the user in order to optimize his profile.

According to this embodiment, the additional perfume $NP_{q+1}$ is chosen among the set of perfumes for which the user did not give any satisfaction note and as being the most relevant perfume for optimizing the user profile. For example, the system takes successively each of the m-q remaining perfumes and computes an expected value of the user profile by successively supposing the 3 or 5 notes for that perfume. Then, the system computes the means value of the 3 or 5 expected set of weighting coefficients for each perfume. Finally, the system chooses the one of the remaining perfume for which the notation will have the most influence on the set of weighting coefficients for the user.

Alternatively, in order to ask the user information about the perfume that will most likely improve the performance of the system, the system computes the following formula:

$$\sum_{j=1}^{n}\left(\sum_{L=1}^{NL} \frac{f(L) \cdot |\alpha_{j,s} - \alpha_{j,s',L}|}{\alpha_{j,s}}\right),$$

where:

NL is the total number of options (preferably 3 or 5) for the opinion L of the user;

$\alpha_{j,s}$ is the set of coefficients $\alpha_j$ already calculated on the basis of the q perfumes already noted by the user;

$\alpha_{j,s',L}$ is the set of coefficients $\alpha_j$ calculated for the set of q+1 perfumes under the hypothesis of a note L for the perfume of rank q+1; and f(L) is an optional function of weighting of the different coefficients $\alpha_j$.

By maximizing the former formula over all the perfumes, it is possible to select the perfume that could potentially lead to the biggest change in the weighting coefficients $\alpha_j$. Such a perfume is the perfume $NP_{q+1}$ that the user will be asked (block 37) to rate in order to maximize the performance of the system. This is a reasonable assumption, as the coefficients $\alpha_j$ completely specify the user profile.

In the example to perfumes, it is more desirable to find perfumes that will change the knowledge of the characteristics of perfumes that are ranked relatively high, rather than those that are ranked relatively low. Therefore, the above function f(L) will bias the search towards perfumes that will change the knowledge of perfumes ranked relatively high. For example, the respective weighting coefficient attributed to each satisfaction note could be f(L)=L if the satisfaction notes L are coded with numerical values (1, 2, 3 or 1, 2, 3, 4, 5), 1 representing the lowest rating.

Having the note of the user for the perfume of rank q+1, the system computes again (block 38) the weighting coefficients $\alpha_j$, taking into account the additional satisfaction note. As in the first simplified embodiment, the user profile is obtained after this step.

The user profile determination is then ended.

The following steps illustrated in FIG. 4 correspond to an exemplary implementation of the method for predicting some preferred (PP1, PP2, PP3) perfumes on the basis of the user's profile.

A first step (bloc 39) consists in estimating the satisfaction notes that the user would have given for all the perfumes not yet rated by the user on the basis of the weighting coefficients determined for that user. Preferably, the estimation step computes also the rated perfumes. This preferred embodiment allows the determination of non-integer notes for all the perfumes, which leads to a more accurate estimation.

The estimating step corresponds to applying the following formula to all the m perfumes:

$$IP_i = \sum_{j=1}^{n} \alpha_j \cdot MV_{i,j},$$

where $IP_i$ designates the note estimated for the perfume $P_i$ of the database, where $\alpha_j$ designates the weighting coefficient of rank j affected to the sensor of rank j of the smell print according to the user's profile, and where $MV_{i,j}$ designates the digital (mean) value of rank j (sensor $S_j$) of the smell print of perfume $P_i$ of rank i.

The next step (block 40) corresponds to select a limited number (at least one) of perfumes that have, for example, the highest ratings, and to deliver (for example, display) the results to the user.

According to a first embodiment, a subset of products close to the highest (or lowest) note with a predetermined margin is then outputted. For example, the margin is fixed at 10%. That means that the products for which the estimated note are higher than 2.7 (in a system with notes from 1 to 3) or 4.5 (in a system with notes from 1 to 5) are outputted as being the most enjoyable products for the user.

According to another embodiment, the number of the outputted products is predetermined. For example, the system proposes the three products {PP1, PP2, PP3} having the highest estimated notes (preferably sorted) as being the most enjoyable products for the user.

An advantage of the present invention is that the weighting coefficients used to establish the user profile can be determined with just a small number (less than 10) of satisfaction notes really given by the user.

Another advantage of the present invention is that the determination of the profile of the user is consistent with an optimization of that profile by proposing an additional notation to the user.

Another advantage of the present invention is that the predicting implementation does not depend upon other users as in conventional systems. Therefore, the method and system of the present invention are particularly efficient.

Another advantage of the present invention is that the method does not depend on the kind of sensors (for example, the groups of chemical compounds for which the sensors are responsive) provided that all the smell or taste prints of the products are obtained with the same set of sensors (responsive to the same groups of chemical compounds). Further, according to a preferred embodiment in which the same electronic nose or tongue is used (i.e. exactly the same sensors) for all the products, the sensors do not need to be calibrated.

It should be noted that the user could also rate basic smells. For example, the set of ratings asked to the user for the perfumes can be completed by ratings for basic smells like coffee, chocolate, spices, flowers, etc.

Another example of application of the present invention concerns predicting the wine preferences of a user. For example, the user is asked to rate some basic smells of wines in order to establish his wine's user profile. Then, the system can work as described above in connection to the perfume application to determine, among a set of wine's characteristics or wines' list, those that would be adapted to the user.

The invention may also apply to taste prediction. For example, asking the user for ratings concerning tastes of several foods, the system can be able to estimate the satisfaction level of that user for other foods contained in a database and for which a taste print has been determined using an electronic tongue.

Of course, smell and taste feelings can be combined (for example for wines).

Having thus described at least one illustrative embodiment of the invention, various alterations modifications and improvements will readily occur to those skilled in the art. Such alteration, modification, and improvements are intended to be within the spirit and scope of the invention. Accordingly, the foregoing description is by way of example only and is not intended to be limiting. The invention is limited only as defined in the following claims and the equivalent thereto.

The invention claimed is:

1. A method for determining a scent or taste profile of a user comprising:

storing in a computerized system for each of a set of products chosen among products for which a database includes smell or taste prints constituted by a set of measurements given by smell or taste electronic sensors, a satisfaction note rating (SN) given by the user;

automatically calculating by the computer weighting coefficients constituting said profile and respectively affected to said sensors measurements, by successive approximation of sets of weighting coefficients leading to minimizing the sum of the quadratic errors over the set of satisfaction notes; and selecting a product based on said weighting coefficients constituting said profile;

wherein the weighting coefficients of the user's profile are determined by minimizing the result of the following formula by successive approximation of sets of weighting coefficients $\alpha_j$, $$\sum_{h=1}^{q} \left( SP_h - \sum_{j=1}^{n} (\alpha_j \cdot MV_{j,h}) \right)^2,$$

where $SN_h$ designates the rating given by the user for the product of rank h of said set of q products, where $\alpha_j$ designates the weighting coefficient of rank j affected to the product of rank j of the smell or taste prints, and where $MV_{j,h}$ designates the scores of rank j of the smell print of product of rank h.

2. The method of claim 1, wherein each satisfaction note rating, is a value from 1 to 5.

3. The method of claim 1, further comprising receiving from the user an additional rating for an additional product selected, on the basis of the already given ratings, as being the product for which the notation of the user will be the most relevant for the user profile.

4. A method for selecting a product adapted to a user on the basis of its smell or taste, using a user profile determined according to any one of claims 1 or 3, the method comprising:
- estimating a rating for products for which the database includes the smell or taste prints, by applying the weighting coefficients to the smell or taste prints; and
- selecting among the products, a subset on the basis of the estimated rating.

5. The method of claim 4, in which the product of said subset is selected for having an estimated rating close to the highest or lowest rating within a predetermined margin.

6. The method of claim 4, in which a predetermined number of products having the highest or lowest estimated rating constitutes said subset.

7. The method of claim 4, applied to perfumes selection.

8. The method of claim 4, applied to wines selection.

9. The method of claim 1, wherein said satisfaction note rating is a value from 1 to 3.

10. A method for selecting a product adapted to a user on the basis of its smell or taste comprising:
- storing in a computerized system for each of a set of products chosen among products for which a database includes smell or taste prints constituted by a set of measurements given by smell or taste electronic sensors, a satisfaction note rating (SN) given by the user;
- automatically calculating by the computer weighting coefficients constituting a user profile and respectively affected to said sensors measurements, by successive approximation of sets of weighting coefficients leading to minimizing the sum of the quadratic errors over the set of satisfaction notes;
- receiving from the user an additional rating for an additional product selected, on the basis of the already given ratings, as being the product for which the notation of the user will be the most relevant for the user profile;
- wherein the selection of the additional product is made by maximizing the following formula over all the products:

$$\sum_{j=1}^{m}\left(\sum_{L=1}^{NL}\frac{f(L)\cdot|\alpha_{j,s}-\alpha_{j,s',L}|}{\alpha_{j,s}}\right),$$

where NL is the total number of values for the ratings L of the user; $\alpha_{j,s}$ is the set of coefficients $\alpha_j$ already calculated on the basis of the q products already noted by the user; $\alpha_{j,s'}$, L is the set of coefficients $\alpha_j$, calculated for the set of q+1 products under the hypothesis of a note L for the product of rank q+1; and f(L) is an optional function of weighting of the different coefficients $\alpha_j$.

11. A method for selecting a product adapted to a user on the basis of its smell or taste comprising:
- storing in a computerized system for each of a set of products chosen among products for which a database includes smell or taste prints constituted by a set of measurements given by smell or taste electronic sensors, a satisfaction note rating (SN) given by the user;
- automatically calculating by the computer weighting coefficients constituting a user profile and respectively affected to said sensors measurements, by successive approximation of sets of weighting coefficients leading to minimizing the sum of the quadratic errors over the set of satisfaction notes;
- estimating a rating for products for which the database includes the smell or taste prints, by applying the weighting coefficients to the smell or taste prints; and
- selecting among the products, a subset of products on the basis of the estimated rating,
- wherein the estimated rating for each product is obtained by applying the following formula:

$$IP_i = \sum_{j=1}^{n} \alpha_j \cdot MV_{i,j},$$

where $IP_i$ designates the note estimated for the product $P_i$ of the database, where $\alpha_j$ designates the weighting coefficient of rank j affected to the product of rank j of the smell or taste print according to the user's profile, and where $MV_{i,j}$ designates the measurement of rank j of the smell or taste print of product of rank i.

12. A system for determining a scent or taste profile of a user comprising:
- a database containing smell or taste prints of products constituted by a set of measurements given by smell or taste electronic sensors;
- a memory element for storing a user rating of each of a set of products chosen among the products contained in said database; and
- a calculator for determining weighting coefficients constituting said profile and respectively affected to said sensors, by successive approximation of sets of weighting coefficients leading to minimizing the sum of the quadratic errors over the set of ratings and for selecting a product based on said weighting coefficients constituting said profile;
- wherein the weighting coefficients of the profile are further determined by the calculator by minimizing the result of the following formula by successive approximation of sets of weighting coefficients $\alpha_j$, $$\sum_{h=1}^{q}\left(SP_h - \sum_{j=1}^{n}(\alpha_j \cdot MV_{j,h})\right)^2,$$

where $SN_h$ designates the rating given by the user for the product of rank h of said set of q products, where $\alpha_j$ designates the weighting coefficient of rank j affected to the product of rank j of the smell or taste prints, and where $MV_{j,h}$ designates the scores of rank j of the smell print of product of rank h.

13. The system of claim 12, further comprising:
- an estimator to determine estimated ratings for products that have their smell or taste print in the database, by applying the weighting coefficients to the smell or taste prints; and
- a selector for selecting among the products, a subset on the basis of the estimated ratings.

14. The system of claim 13, wherein said products are perfumes or wines.

15. The system of claim 13, wherein said selector is configured to select a subset of products having estimated ratings within a predetermined margin of the highest or lowest estimated rating.

16. The system of claim 12, further comprising a smell or taste electronic sensor.

17. A system for selecting a product adapted to a user on the basis of its smell or taste, using a user profile, comprising:
- a database containing smell or taste prints of products constituted by a set of measurements given by smell or taste electronic sensors;
- a memory element for storing a user rating of each of a set of products chosen among the products contained in said database; and
- a calculator for determining weighting coefficients constituting said profile and respectively affected to said sensors, by successive approximation of sets of weighting coefficients leading to minimizing the sum of the quadratic errors over the set of ratings; for estimating a rating for products for which the database includes the smell or taste prints, by applying the weighting coefficients to the smell or taste prints; and for selecting among the products, a subset of the products on the basis of the estimated rating, wherein the estimated rating for each product is obtained by the calculator by applying the following formula:

$$IP_i = \sum_{j=1}^{n} \alpha_j \cdot MV_{i,j},$$

where $IP_i$ designates the note estimated for the product $P_i$ of the database, where $\alpha_j$ designates the weighting coefficient of rank j affected to the product of rank j of the smell or taste print according to the user's profile, and where $MV_{i,j}$ designates the measurement of rank j of the smell or taste print of product of rank i.

* * * * *

UNITED STATES PATENT AND TRADEMARK OFFICE
CERTIFICATE OF CORRECTION

PATENT NO.          : 7,587,331 B2                                    Page 1 of 1
APPLICATION NO.     : 10/615157
DATED               : September 8, 2009
INVENTOR(S)         : Pelletier It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1746 days.

Signed and Sealed this
Ninth Day of August, 2011

David J. Kappos
*Director of the United States Patent and Trademark Office*